(12) United States Patent
Goode et al.

(10) Patent No.: US 9,936,965 B2
(45) Date of Patent: Apr. 10, 2018

(54) SNARE SYSTEM

(71) Applicant: Cook Medical Technologies LLC, Bloomington, IN (US)

(72) Inventors: Louis B. Goode, Cranberry Township, PA (US); Chun Kee Lui, Apollo, PA (US); Michael Wayne Emmert, Apollo, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 694 days.

(21) Appl. No.: 13/623,355

(22) Filed: Sep. 20, 2012

(65) Prior Publication Data
US 2013/0079758 A1    Mar. 28, 2013

Related U.S. Application Data

(60) Provisional application No. 61/538,418, filed on Sep. 23, 2011.

(51) Int. Cl.
*A61B 17/00* (2006.01)
*A61B 17/221* (2006.01)
(Continued)

(52) U.S. Cl.
CPC ...... *A61B 17/221* (2013.01); *A61B 2017/003* (2013.01); *A61B 2017/0046* (2013.01);
(Continued)

(58) Field of Classification Search
CPC .......... A61B 2017/0046; A61B 17/221; A61B 2017/003; A61B 2017/2212;
(Continued)

(56) References Cited

U.S. PATENT DOCUMENTS

| 5,380,304 A | | 1/1995 | Parker ........................... 604/282 |
| 5,669,933 A | * | 9/1997 | Simon et al. ................. 600/200 |

(Continued)

FOREIGN PATENT DOCUMENTS

| EP | 1 849 422 A2 | 10/2007 | ............. A61B 17/28 |
| WO | WO 98/19608 | 5/1998 | ............. A61B 17/22 |
| WO | WO 03/073961 A1 | 9/2003 | ............... A61F 2/01 |

OTHER PUBLICATIONS

International Search Report and Written Opinion, dated Dec. 14, 2012, issued in PCT Application No. PCT/US2012/056256, pp. 1-12, International Searching Authority, European Patent Office, Rijswijk, The Netherlands.

*Primary Examiner* — Scott T Luan
(74) *Attorney, Agent, or Firm* — Brinks Gilson & Lione

(57) ABSTRACT

A snare for deployment or retrieval of an implantable medical apparatus. The snare includes a shaft, and a tip distal of the shaft. The tip includes an extendable member capable of self-centering the implantable apparatus during a deployment or retrieval. The extendable member is selectively receivable in the tip, distally extendable from the tip, and rotatable relative to the tip. An activatable handle is engaged with the shaft. A wire has an end engaged with the handle and an end engaged with the tip. Upon activation, the wire is urged in a proximal direction, resulting in a flexure of the tip. An elongated mechanism has a proximal portion engaged with the handle, and a distal portion engaged with the tip extendable member. The elongated mechanism is configured for selectively controlling the receiving, deploying, and rotating of the extendable member.

18 Claims, 15 Drawing Sheets

(51) Int. Cl.
    *A61B 17/29*      (2006.01)
    *A61B 17/22*      (2006.01)

(52) U.S. Cl.
    CPC .............. *A61B 2017/00358* (2013.01); *A61B 2017/2212* (2013.01); *A61B 2017/22035* (2013.01); *A61B 2017/2929* (2013.01)

(58) Field of Classification Search
    CPC .. A61B 2017/00358; A61B 2017/2929; A61B 2017/22035
    See application file for complete search history.

(56) References Cited

U.S. PATENT DOCUMENTS

| | | | |
|---|---|---|---|
| 2003/0144672 A1* | 7/2003 | Gellman et al. | 606/127 |
| 2006/0235431 A1 | 10/2006 | Goode et al. | 606/108 |
| 2007/0088418 A1 | 4/2007 | Jacobson | 607/116 |
| 2007/0186933 A1* | 8/2007 | Domingo et al. | 128/207.15 |
| 2008/0071342 A1 | 3/2008 | Goode et al. | 607/122 |
| 2008/0228135 A1 | 9/2008 | Snoderly | 604/95.04 |
| 2009/0163926 A1* | 6/2009 | Sos | 606/108 |
| 2013/0267848 A1* | 10/2013 | Fearnot et al. | 600/439 |

* cited by examiner

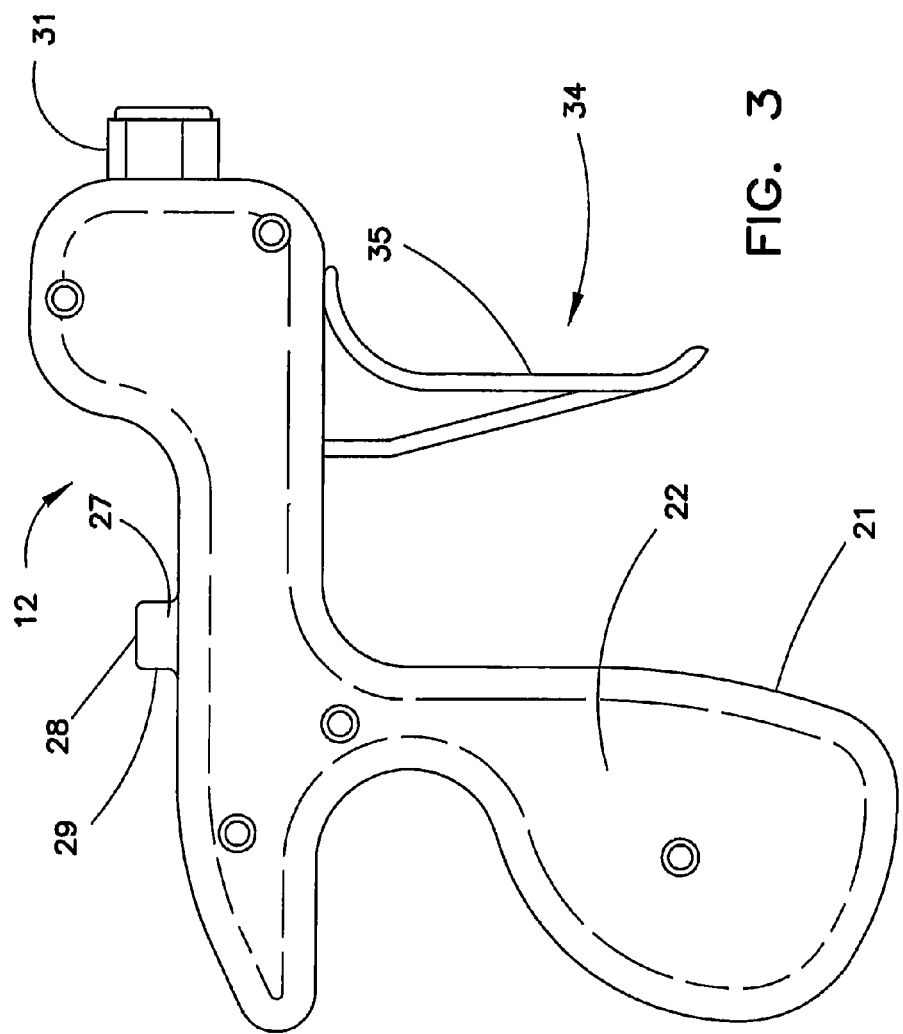

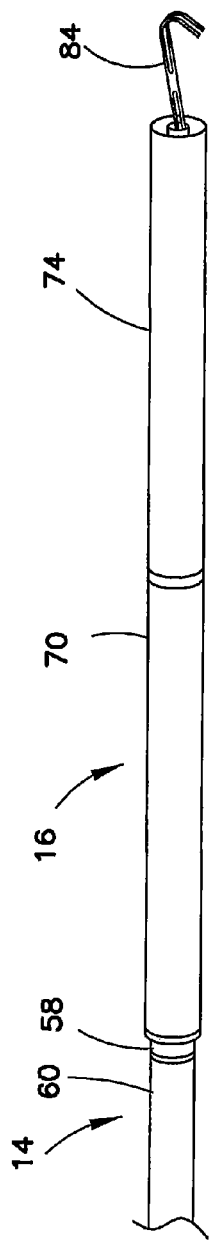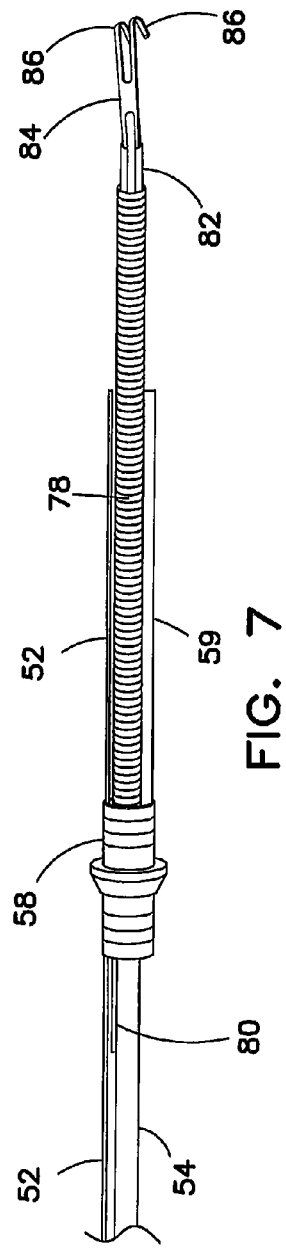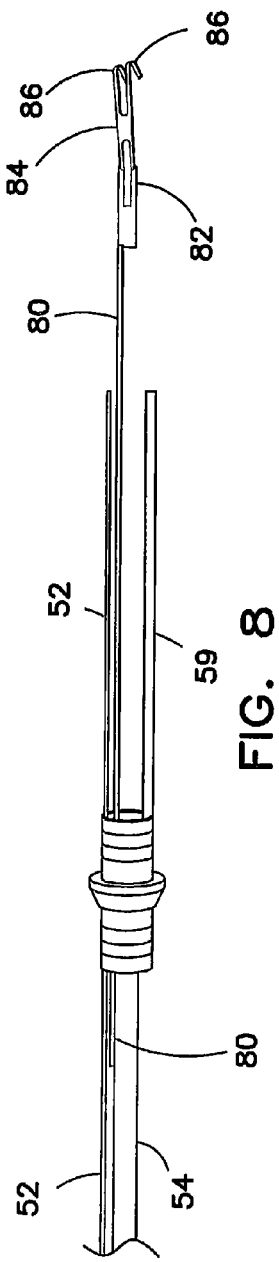

SNARE SYSTEM

RELATED APPLICATION

The present patent document claims the benefit of the filing date under 35 U.S.C. § 119(e) of Provisional U.S. Patent Application Ser. No. 61/538,418, filed Sep. 23, 2011, which is hereby incorporated by reference.

BACKGROUND

1. Technical Field

This invention relates to a snare for use with an implantable medical apparatus. More particularly, the invention relates to a system comprising a snare and an implantable medical apparatus, wherein the snare is capable of delivering the implantable medical apparatus to a target site within the body of a patient, and/or retrieving the implanted medical apparatus from the body of the patient.

2. Background Information

Implantable medical apparatuses structured for carrying out a desired medical activity are often percutaneously delivered to a target site within the body of a patient for implantation. The implantable medical apparatus is typically delivered to the target site in a device capable of traversing the interior anatomy of the patient, and deploying the apparatus at the target site.

Once the intended medical activity has been completed or is deemed of no further benefit to the patient, or if the implanted apparatus becomes inoperable, it is generally desirous to remove the apparatus from the body of the patient. Devices for retrieving implanted medical apparatuses are known in the medical arts. While some of these devices are suitable for retrieving certain implanted apparatuses, and/or for retrieving apparatuses implanted at certain areas of the anatomy, such devices may be less suitable for retrieving other apparatuses, and/or for retrieving apparatuses from other hard-to-reach areas of the anatomy. In addition, most such retrieval devices are not also suitable for initially deploying the apparatus intended for implantation. In this instance, a separate deployment device would be required.

Some prior art implanted apparatuses are provided with an extended, or necked, portion at the proximal end of the apparatus. The extended portion may have a knob or like structure at the proximal end of the extended portion. A looped-type snare may be introduced through the body passageway and closed around the extended portion. In this case, the apparatus is removed as the snare is withdrawn through the body passageway. One example of such a removal device is disclosed in U.S. Pat. Publ. No. 2009/0163926, incorporated by reference herein. Alternatively, a grasping device may be introduced to snag or otherwise grasp the knob, and the apparatus is withdrawn through the passageway.

When the implanted apparatus is withdrawn via a loop-type snare, a grasping device, or like structure, the apparatus is subject to sway or other lack of control as it is pulled or otherwise withdrawn along the body passageway. In addition, in known removal devices of the type in which the implanted apparatus is withdrawn into a sheath of the removal device prior to removal of the device from the body passageway, the lack of control hinders the ability to efficiently withdraw the apparatus into the sheath.

It would be desirable to provide a device capable of retrieving an implanted medical apparatus from an interior site in the anatomy of the patient that overcomes many of the difficulties encountered with prior art devices. In addition, it would be desirable to provide a system comprising a device and a complementary implantable medical apparatus, wherein the device is configured relative to the implantable apparatus such that the device could be used for delivering the apparatus to a target site within the body of a patient for implantation, and/or retrieving the implanted apparatus from the body of the patient.

BRIEF SUMMARY

The problems of the prior art are addressed by the features of the present invention. In one form thereof, the invention comprises a snare for use with an implantable medical apparatus. An elongated shaft has a proximal end, a distal end, and a passageway extending therethrough. A tip has a proximal end, a distal end, and a passageway extending therethrough. The tip passageway is aligned with the shaft passageway and sized such that the implantable apparatus is receivable therein. A length of the tip is capable of flexure. The tip proximal end is engaged with the shaft distal end, and the tip includes an extendable member configured for engagement with the implantable apparatus. The extendable member is selectively receivable in the tip passageway, deployable in a distal direction from the tip passageway, and rotatable relative to the tip passageway. A handle having an activator is configured for engagement with the shaft proximal end. A wire member has a proximal end engaged with the handle activator, and a distal end engaged with the tip length capable of flexure. The wire member is movable for flexure of the tip length upon a movement of the activator. An elongated mechanism has a proximal portion engaged with the handle, and a distal portion engaged with the tip extendable member. The elongated mechanism is configured for selectively controlling the receiving, deploying, and rotating of the extendable member.

In another form thereof, the invention comprises a snare system. An implantable medical apparatus includes a main body portion and a graspable structure extending from the main body portion. A snare is configured for at least one of deploying the medical apparatus to an interior body surface of a patient, and retrieving the medical apparatus from the interior body surface. The snare includes an elongated shaft having a proximal end, a distal end, and a passageway extending therethrough, and a tip having a proximal end, a distal end, and a passageway extending therethrough. The tip passageway is aligned with the shaft passageway and sized such that the implantable apparatus is receivable therein. A proximal length of the tip is capable of flexure, and the tip proximal end is engaged with the shaft distal end. The tip includes an extendable member configured for engagement with the graspable structure of the implantable apparatus. The extendable member is selectively receivable in the tip passageway, deployable in a distal direction from the tip passageway, and rotatable relative to the tip passageway. A handle is configured for engagement with the shaft proximal end, wherein the handle includes an activator. A wire member has a proximal end engaged with the handle activator and a distal end engaged with the tip length capable of flexure. The wire member is movable in a proximal direction for flexure of the tip length upon a movement of the activator. An elongated mechanism has a proximal portion engaged with the handle, and a distal portion engaged with the tip extendable member. The elongated mechanism is configured for selectively controlling the receiving, deploying, and rotating of the extendable member.

In yet another form thereof, the invention comprises a medical assembly. The medical assembly includes an implantable medical apparatus, and a device configured for deploying the medical apparatus to an interior surface of a patient and/or retrieving the medical apparatus from the interior body surface. The implantable medical apparatus comprises a main body portion, a neck portion extending in a proximal direction from the main body portion, and a larger diameter element at a proximal end of the neck portion. The larger diameter element has opposing longitudinal sides. The device includes an elongated shaft having a proximal end, a distal end, and a passageway extending therethrough; and a tip having a proximal end, a distal end, and a passageway extending therethrough. The tip passageway is aligned with the shaft passageway and sized such that the implantable apparatus is receivable therein. A length of the tip is capable of flexure, and the tip proximal end is engaged with the shaft distal end. The tip includes an extendable member selectively receivable in the tip passageway, deployable in a distal direction from the tip passageway, and rotatable relative to the tip passageway. The extendable member comprises a first engagement element configured for controllably engaging a first one of the opposing sides of the larger diameter element, and a second engagement element for controllably engaging a second one of the opposing sides of the larger diameter element, wherein the controllable engagement is suitable for self-centering the implantable medical apparatus relative to the tip passageway. The device includes a handle configured for engagement with the shaft proximal end; and a wire member engageable with the handle. A proximal end of the wire member is engaged with the handle, and a distal end is engaged with the tip length capable of flexure. The wire member is movable in a proximal direction for flexure of the tip length upon a movement of the handle. An elongated mechanism has a proximal portion engaged with the handle and a distal portion engaged with the tip extendable member. The proximal portion comprises a pusher member and the distal portion comprises a bendable coil. The elongated mechanism is configured for selectively controlling the receiving, deploying, and rotating of the extendable member for effecting the controlled engagement of respective engagement elements with the opposing sides of the larger diameter element of the implantable medical apparatus.

BRIEF DESCRIPTION OF THE DRAWINGS

FIG. 3 is a side view of the handle mechanism of the snare of FIG. 1;

FIG. 6 is an enlarged side view of the tip portion in the generally linear configuration;

FIG. 7 is an enlarged side view of the tip portion as in FIG. 6, wherein the sheath, retriever flex tube, and retrieving tip have been omitted to illustrate the underlying structure;

FIG. 8 is an enlarged side view similar to that of FIG. 7, wherein the flex coil has been omitted to illustrate the underlying structure;

DETAILED DESCRIPTION OF THE DRAWINGS AND THE PRESENTLY PREFERRED EMBODIMENTS

Figure 1:
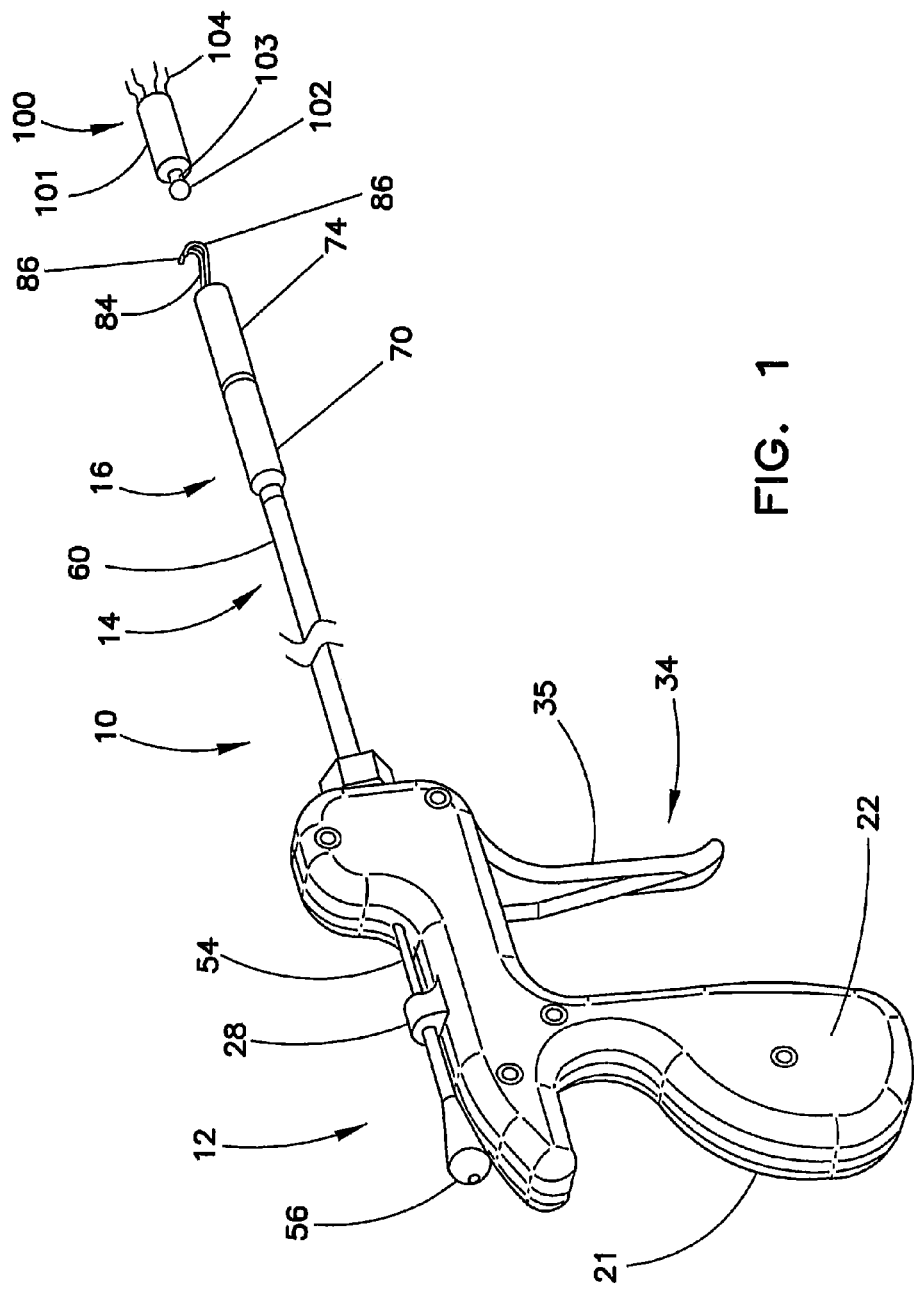
FIG. 1 is a perspective view of a snare according to an embodiment of the present invention, with the distal end of the snare in a generally linear configuration.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is understood that like-referenced numerals are used throughout the Figures to designate similar components.

In the following discussion, the terms "proximal" and "distal" will be used to describe the opposing axial ends of the snare system, as well as the axial ends of other component features of the snare system. The term "proximal" is used in its conventional sense to refer to the end of the snare system, or component thereof, that is closest to the operator during use of the snare. The term "distal" is used in its conventional sense to refer to the end of the snare system, or component thereof, that is initially inserted into the patient, or that is closest to the patient during use.

FIG. 1 is a perspective view of a snare 10 according to an embodiment of the present invention. Snare 10 may be used for retrieving an implanted medical apparatus 100 from within the body of a patient and/or for delivering a medical apparatus to a target site for implantation within the body of the patient.

As shown in FIG. 1, snare 10 includes a handle mechanism 12, a shaft portion 14, and a tip portion 16. As described herein, tip portion 16 is maneuverable between the generally linear configuration shown in FIG. 1 and the curved configuration shown in FIG. 2. Tip portion 16 includes an extendable member at its distal end for engagement with the implanted medical apparatus. In the example shown in FIG. 1, the extendable member comprises a hook member, such as dual-prong hook member 84. Those skilled in the art will appreciate that although dual-prong hook member 84 as shown herein is one example of an extendable member useful in snare 10, other structures capable of self-centering the implanted apparatus (as further described herein) may be substituted.

Figure 2:
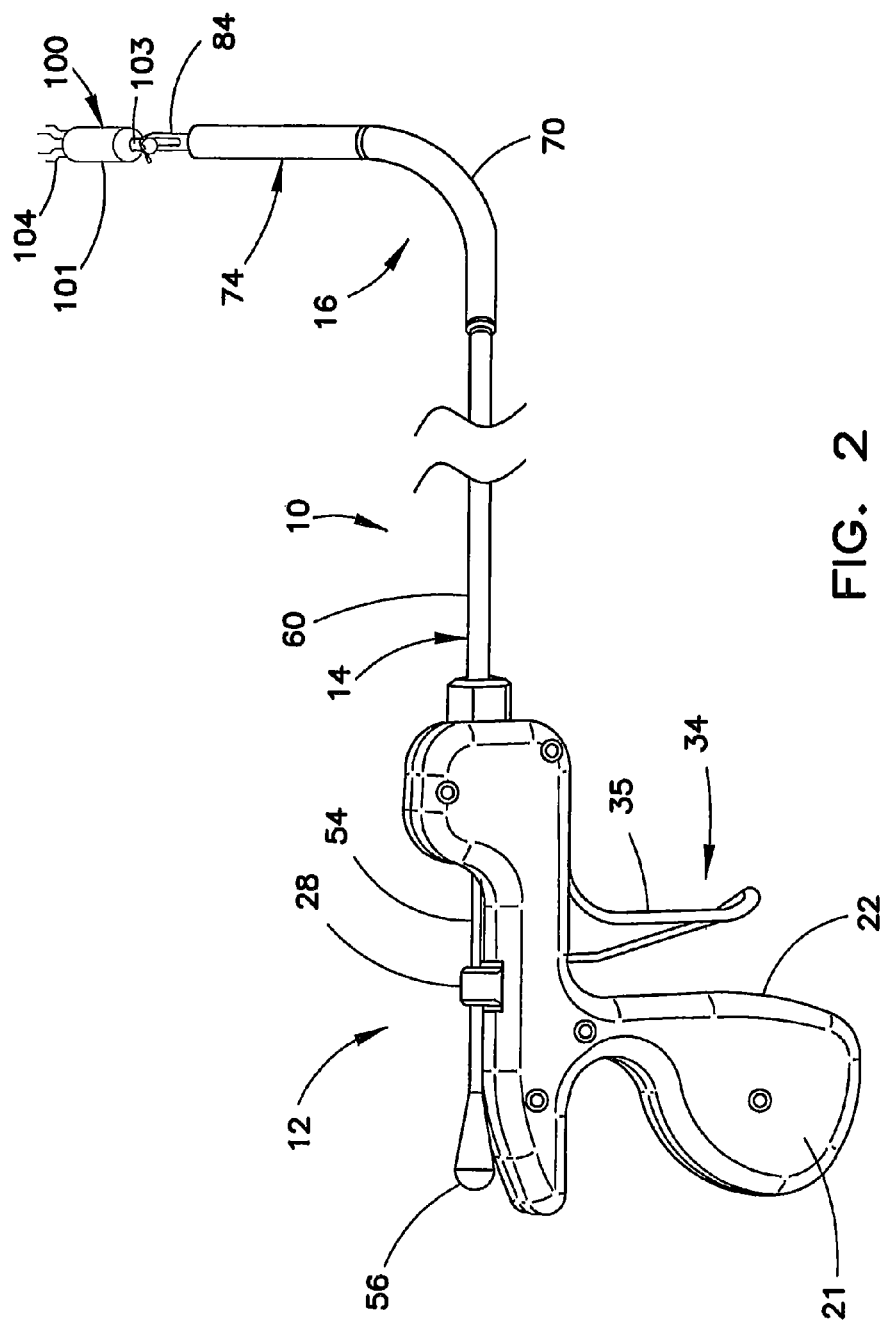
FIG. 2 is a perspective view of the snare of FIG. 1, with the distal end of the snare in a curved, or flex, configuration.

FIG. 1 also illustrates an implanted medical apparatus 100 spaced from snare 10, and more particularly, from the hook member 84. In FIG. 2, the implanted medical apparatus 100 is shown engaged by the prongs of the hook member. In the example shown, implanted medical apparatus 100 comprises a generally cylindrical main body 101. In this non-limiting example, apparatus 100 has legs 104 or like structure extending from the distal end of main body 101, a smaller diameter extended neck portion 103 extending from the proximal end of main body 101, and a larger diameter element 102 at the proximal end of smaller diameter extended portion 103. As further described herein, extended portion 103 and larger diameter element 102 are configured to be engaged by the dual prongs 86 of hook member 84.

Those skilled in the art will appreciate that implanted medical apparatus 100 is only one example of an apparatus that may be engaged with hook member 84, and that other suitable apparatuses may be substituted, provided that any such apparatuses include proximal structure dimensioned in a manner suitable for grasping by the extendable member, such as hook member 84. The implanted medical apparatus 100 may comprise, for example, a vena cava filter, a stent, a cardiac device (e.g., a pacemaker), or other device that is implanted into body tissue of a patient for a medical or diagnostic purpose. In FIGS. 1 and 2, a vena cava filter having legs 104 is illustrated as one non-limiting example.

Figure 4A:
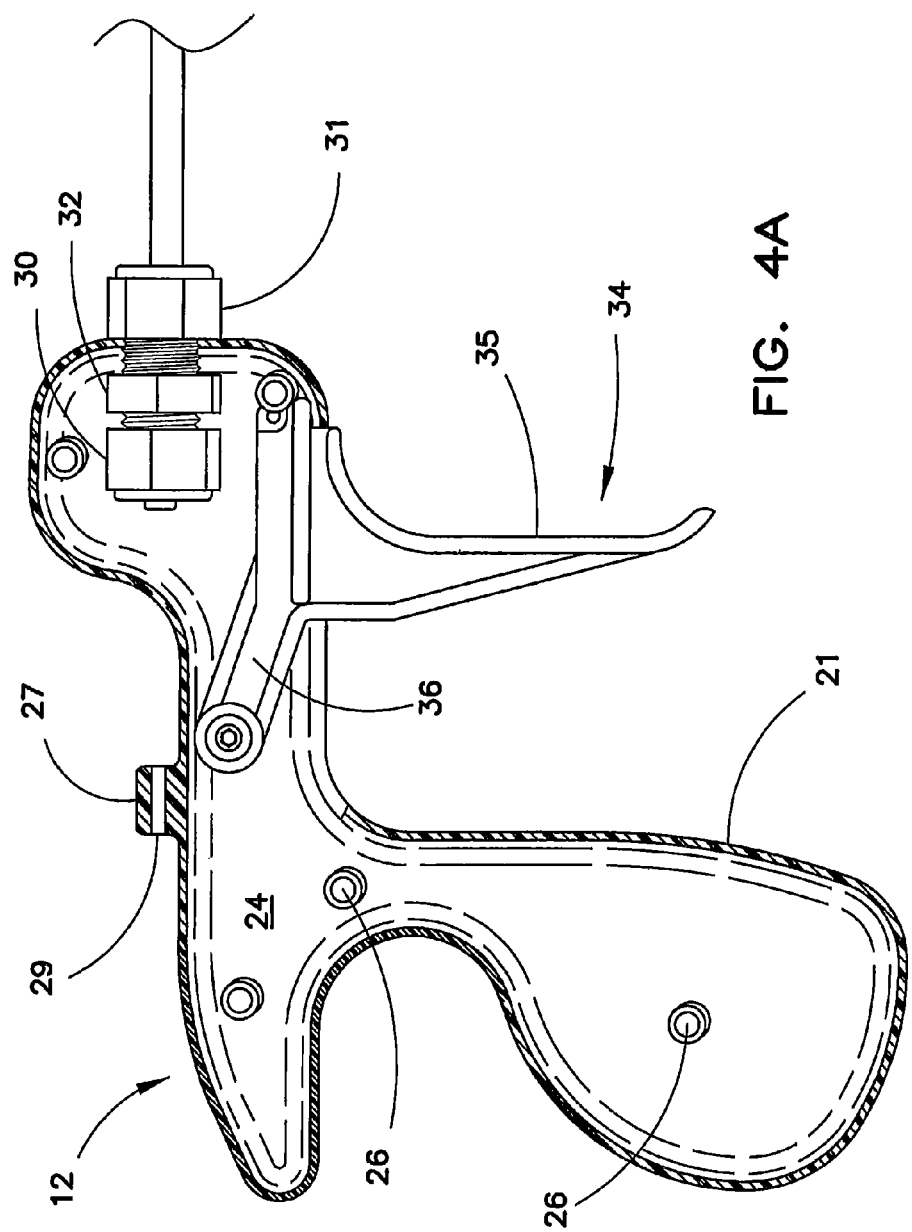
FIG. 4A is a side view of the handle mechanism in the configuration of FIG. 1, with a side wall removed to illustrate the interior structure of the handle mechanism.
Figure 4B:
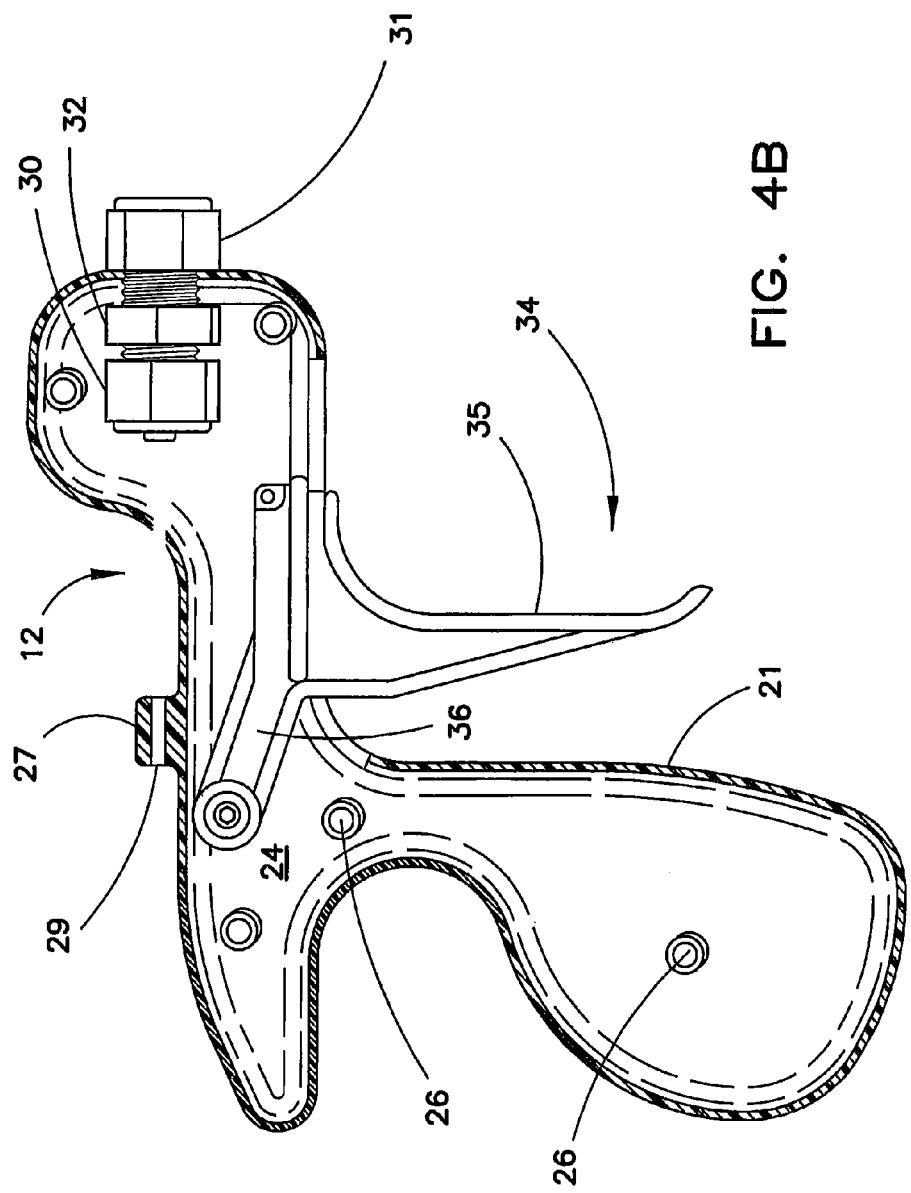
FIG. 4B is a side view of the handle mechanism in the configuration of FIG. 2, with a side wall removed.

FIGS. 3, 4A, and 4B illustrate one embodiment of handle mechanism 12. Handle mechanism 12 includes handle walls 22, 24. FIG. 3 illustrates a side view of the handle mechanism 12, illustrating handle side wall 22. FIGS. 4A and 4B illustrate handle mechanism 12 with side wall 22 removed to illustrate the interior of handle mechanism 12 and opposite handle wall 24. Handle walls 22, 24 may be connected via a snap fit or other conventional engagement mechanism. In the embodiment shown, handle wall 24 includes a plurality of transverse pegs 26 (FIGS. 4A, 4B) that are received in corresponding receptacles (not shown) on the inside surface of handle wall 22. Handle walls 22, 24 may be formed of a generally rigid composition, such as the plastics DELRIN®, ABS and various polycarbonates. Handle mechanism 12 may be provided with an ergonomically shaped grip 21, as shown in the figures.

Handle mechanism 12 includes an activating member, namely trigger 34. Trigger 34 includes a conventional trigger grip 35 and a proximal trigger extender 36. Trigger extender 36 is configured to receive an end of the retriever pull wire 52 (FIG. 5), as further described herein. Trigger extender 36 is positioned within handle mechanism 12 in a manner to ensure smooth proximal and distal movement of the trigger grip without bending or flexing.

Each handle half includes a tab half 27. Respective tab halves 27 are joined in the assembled handle to form tab 28. Tab halves 27 are configured such that an axial channel 29 is defined therethrough in tab 28 upon joinder of the respective tab halves.

FIG. 4A illustrates the position of trigger 34 in the forward, or at-rest, position. FIG. 4B illustrates the position of trigger 34 after trigger grip 35 has been activated, as described herein. An optional strain relief mechanism may be provided to inhibit kinking of the shaft during use of device 10. In this embodiment, the strain relief mechanism includes interior 30 and exterior 31 strain relief nuts that are joined by adapter 32. Tab 28 and strain relief elements 30, 31, 32 are configured and aligned in handle 12 so that pusher 54 (FIG. 5) can slide through the tab and strain relief elements, as described herein.

Figure 5:
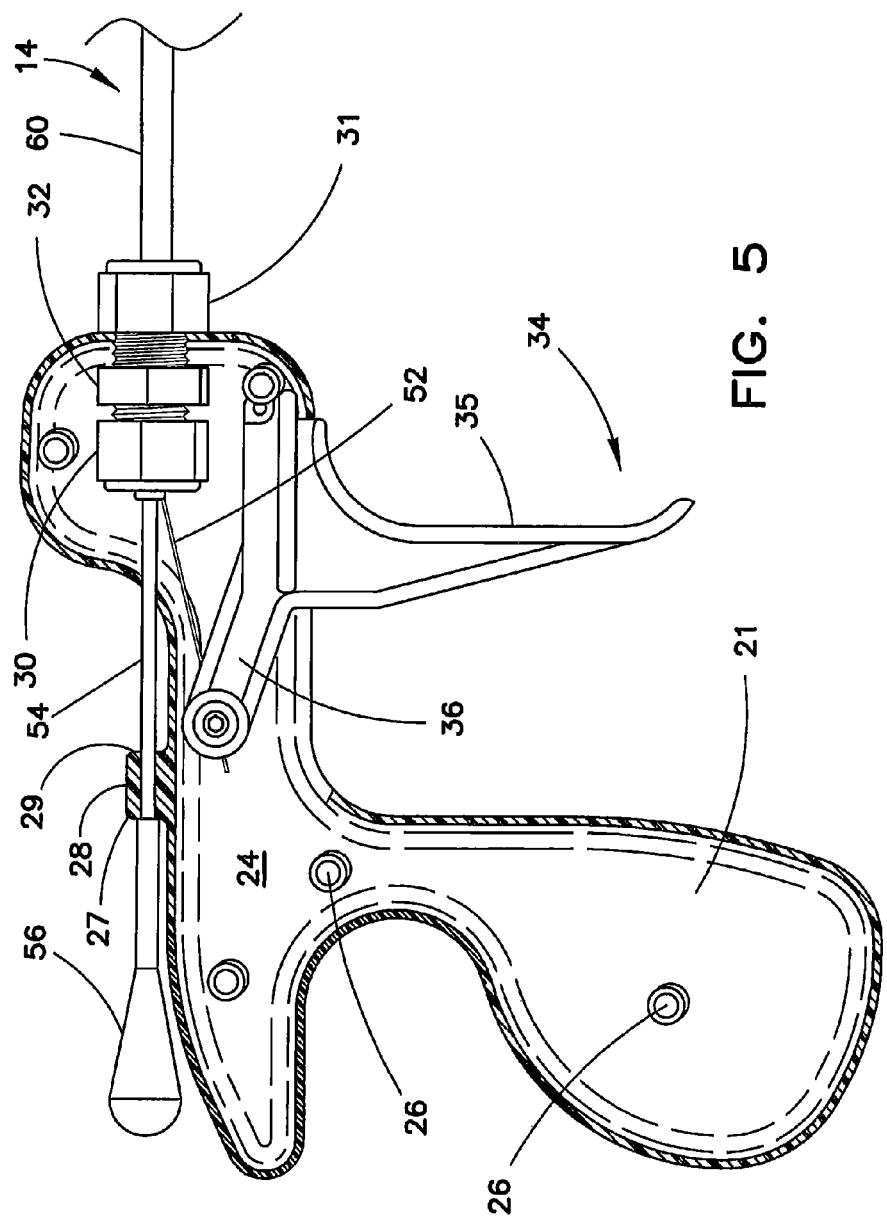
FIG. 5 is a side view of the proximal portion of the snare with a handle side wall removed, including additional features of the snare that interact with the handle mechanism during use of the snare.

FIG. 5 illustrates a side view of the proximal portion of snare 10. As in FIG. 4, handle wall 22 has been removed to allow the interior of the handle to be visualized. This figure differs from FIG. 4A in that additional features of the snare that interact with the handle mechanism during use of the snare are illustrated. As described above, pusher 54 is received along tab axial channel 29. In addition, the proximal end of retriever pull wire 52 is fixedly engaged with trigger extender 36. The distal end of pull wire 52 extends interiorly of shaft portion 14 to, e.g., an attachment point with retriever flex tube 70 (FIGS. 6-8) along an interior surface of the tube.

Shaft portion 14 comprises a sheath member 60. Preferably, sheath member 60 comprises a layered sheath structure having an outer jacket, a reinforcing member such as a braid or a coil, and an inner liner. In one embodiment, the outer jacket may comprise a polyether block amide, such as PEBAX®, or a polyamide, such as nylon. The reinforcing member may comprise a braided material formed of a metal or metallic alloy such as stainless steel, and the inner liner may comprise nylon. Those skilled in the art will appreciate that other sheath materials may be substituted for those described, and that other conventional sheaths used in the medical field may also be substituted. Sheaths for medical use are well known in the medical arts, and one of ordinary skill in the art can readily form, or obtain, a suitable sheath for use herein. Numerous patent references teach fabrication of sheaths, such as U.S. Pat. No. 5,380,304, incorporated by reference herein.

As stated above, pusher 54 extends through sheath 60. Preferably, pull wire 52 and pusher 54 extend side-by-side (FIG. 7) along an inner passageway extending through sheath 60. The proximal end of pusher 54 extends through channel 29 of tab 28, and is received in a grasping device, such as manipulation knob 56.

FIG. 6 illustrates an enlarged view of the distal portion of snare 10. Distal tip portion 16 comprises retriever flex tube 70, and a retrieving tip 74. In the embodiment shown, the proximal end of retriever flex tube 70 and the distal end of sheath 60 are engaged, e.g., via retriever union 58 (FIGS. 6, 7). A small diameter proximal end of retrieving tip 74 may be received (e.g., via a threaded connection) within the passageway at the distal end of retriever flex tube 70.

Preferably, retriever flex tube 70 is formed of a flexible composition, such as silicone or PTFE, that enables flex tube 70 to flex, or bend, while in the body passageway. In a preferred arrangement, retrieving tip 74 is formed of a more rigid material than flex tube 70, such as stainless steel or titanium.

As shown in FIG. 7, a retriever flex element, such as flex coil 78, extends along the interior of the retriever flex tube 70 and the retrieving tip 74 of tip portion 16. Retriever flex coil 78 may be made of conventional construction, such as stainless steel. The sheath 60, retriever flex tube 70 and retrieving tip 74 have been omitted from FIG. 7 to illustrate the underlying structure. Retriever union 58 engages the distal end of pusher 54 and the proximal end of retriever flex coil 78. The distal end of retriever flex coil 78 is operatively engaged with extendable member 84, e.g., either by direct engagement or indirect engagement via a pusher 82 (FIGS. 7, 8).

As best shown in FIG. 8, a proximal end of a bend tab 59 is attached to retriever union 58. Bend tab 59 extends exteriorly of flex coil 78 in a distal direction from retriever union 58, for controlling a bending of coil 78. The distal end of bend tab 59 is fixed substantially at the proximal end of retrieving tip 74. Bend tab 59 may be formed of a generally rigid composition, such as stainless steel, titanium, or nitinol. Retriever pull wire 52 also extends exteriorly of flex coil 78, and is disposed substantially opposite bend tab 59 along the length of the flex coil.

A stabilizing wire 80 extends through the retriever flex coil 78. The retriever flex coil has been omitted from FIG. 8 to more clearly illustrate the remaining features. The proximal end of stabilizing wire 80 is engaged with retriever union 58. The distal end of stabilizing wire 80 is received in or otherwise engaged with pusher 82, as shown in FIG. 8. Stabilizing wire 80 minimizes the degree of stretch that flex coil 78 may undergo upon flexure. Both pull wire 52 and stabilizing wire 80 may be formed of generally rigid compositions known for such use, such as stainless steel.

The proximal end of hook member 84 is received in or otherwise affixed to the distal end of pusher 82 in any conventional fashion (FIGS. 7, 8). The distal end of hook member 84 includes structure for engagement with the implanted medical device. In the illustrated embodiment, hook member 84 includes two curved hook prongs 86. Hook prongs 86 are configured to capture, or snare, the larger diameter element 102 that is formed or otherwise affixed on the proximal end of the small diameter neck portion 103 of the implanted device.

Hook member 84 is preferably formed of a composition, such as stainless steel, titanium, nitinol, and the like, that renders the hook member visible under medical imaging techniques, such as x-ray and/or ultrasound. Those skilled in the art will appreciate that these are only examples of possible compositions that are suitable for this purpose, and that other appropriate compositions may be substituted for the examples provided above.

The structure of snare 10 may be further understood upon a discussion of one example of its operation. This example describes use of the inventive snare in the retrieval of an implanted medical apparatus from the body of the patient. Those skilled in the art will appreciate that snare 10 may alternatively be used to deliver and implant a medical apparatus at a target site.

Figure 9:
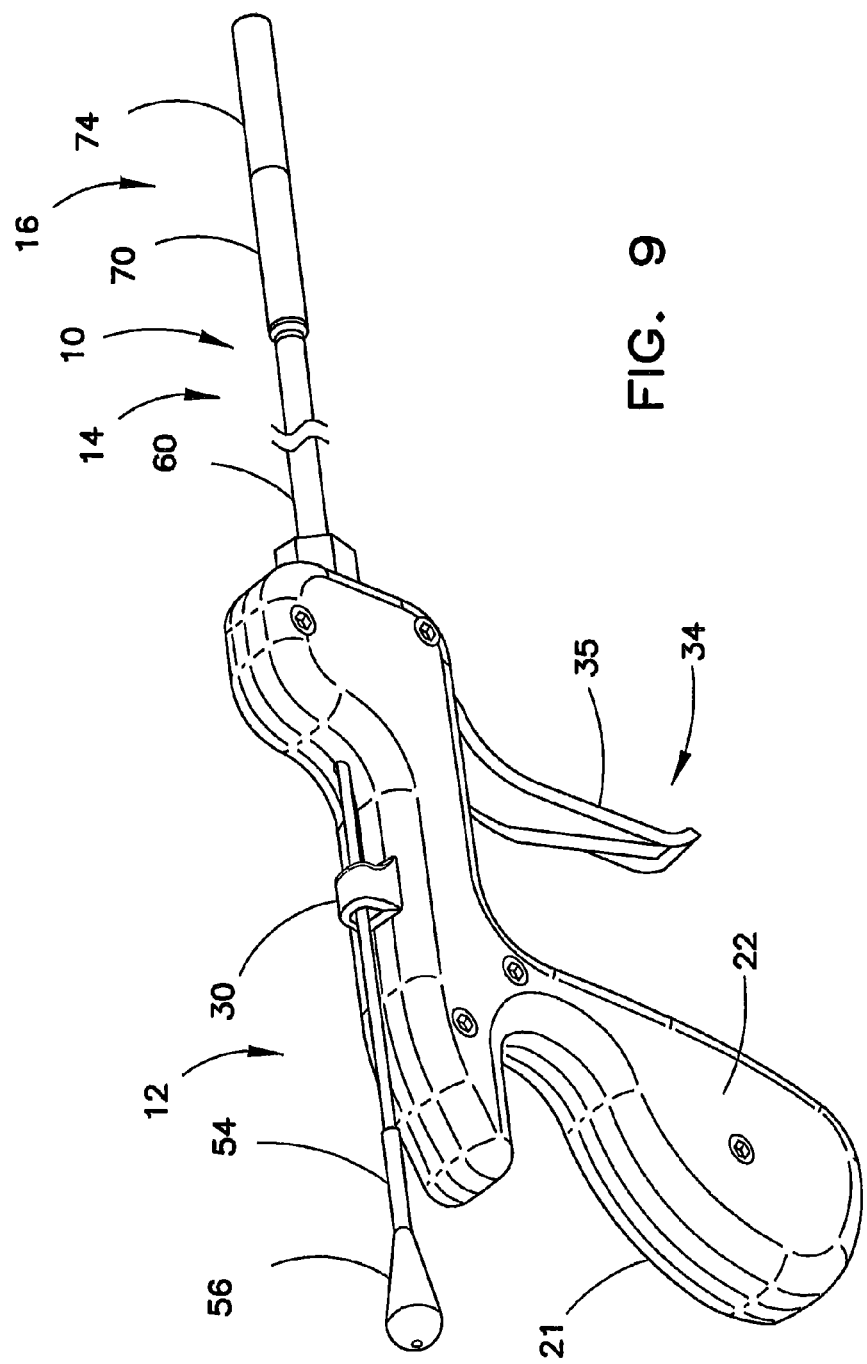
FIG. 9 illustrates the respective initial positions of the handle mechanism and tip portion.

FIG. 9 illustrates the respective initial positions of the handle 12 and tip portion 16 of snare 10. In this position, the distal end of tip portion 16 is initially inserted into a body channel, such as the vasculature, for passage, e.g., under fluoroscopy or ultrasound, to a target site. Manipulation knob 56 is fully retracted in the proximal direction, and the trigger grip 35 is in its fully forward (at rest) position. The tip portion (e.g., retriever flex tube 70 and retrieving tip 74) has a generally linear configuration. The hook member is fully retracted within retrieving tip 74, and is therefore not visible in this figure.

Figure 10:
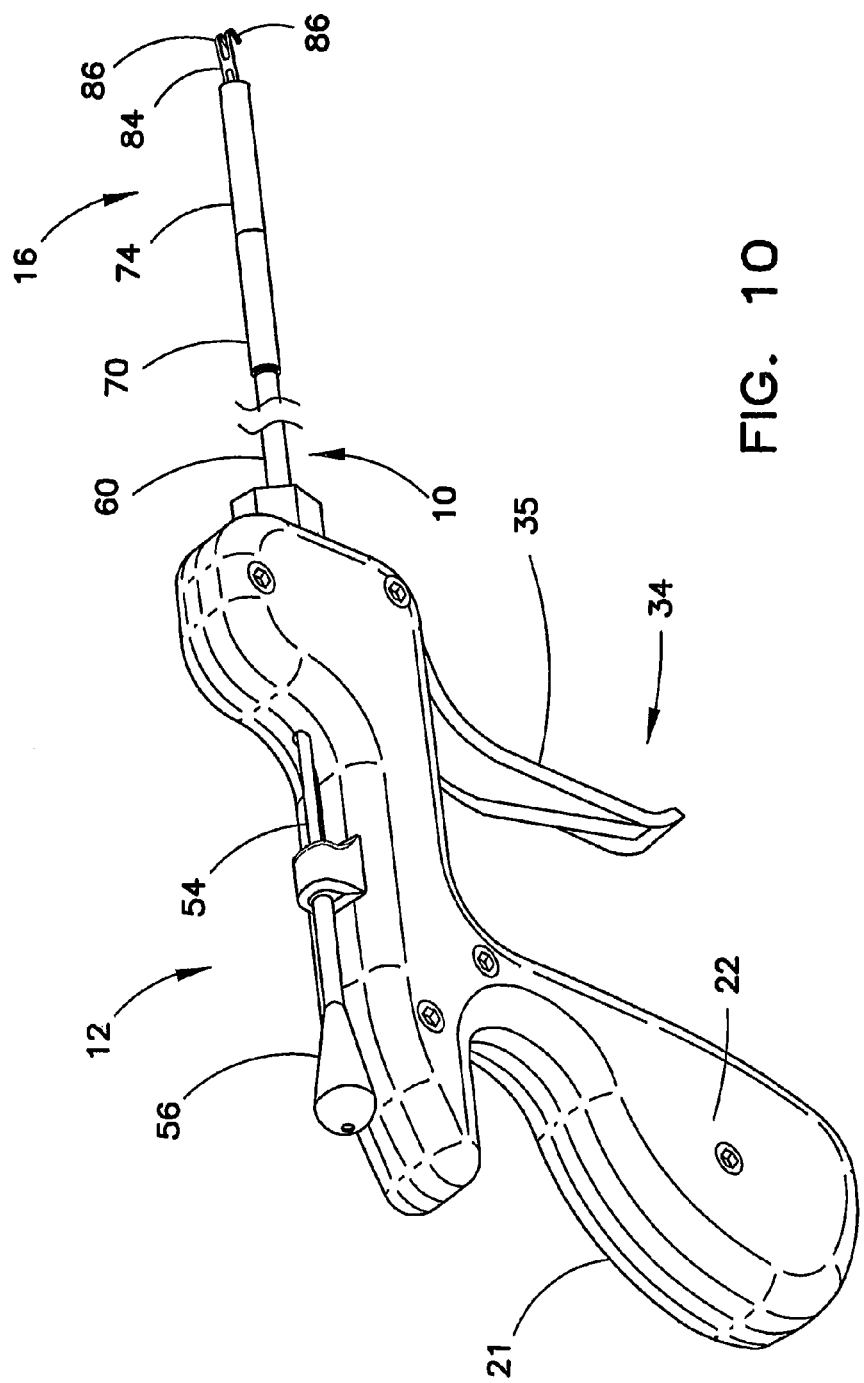
FIG. 10 illustrates the handle mechanism and tip portion in the positions shown in FIG. 9, wherein the manipulation knob has been advanced to an engaged position and the hook member has been deployed from the distal tip portion.

Once the distal end of snare 10 reaches the site of the implanted apparatus, manipulation knob 56 is advanced in the distal direction, as shown in FIG. 10. Upon advancement of manipulation knob 56, pusher 54, flex coil 78, stabilizing wire 80, and pusher 82 are advanced in the distal direction. As a result, hook member 84 is deployed from the distal end of retrieving tip 74 as shown. At this time, retriever flex tube 70 and retrieving tip 74 are maintained in the generally linear configuration as shown in FIG. 9. Manipulation knob 56 may be rotated, advanced, and/or withdrawn as desired to rotate, and thereby position, hook prongs 86 into a suitable position to snare the implanted apparatus 100.

Figure 11:
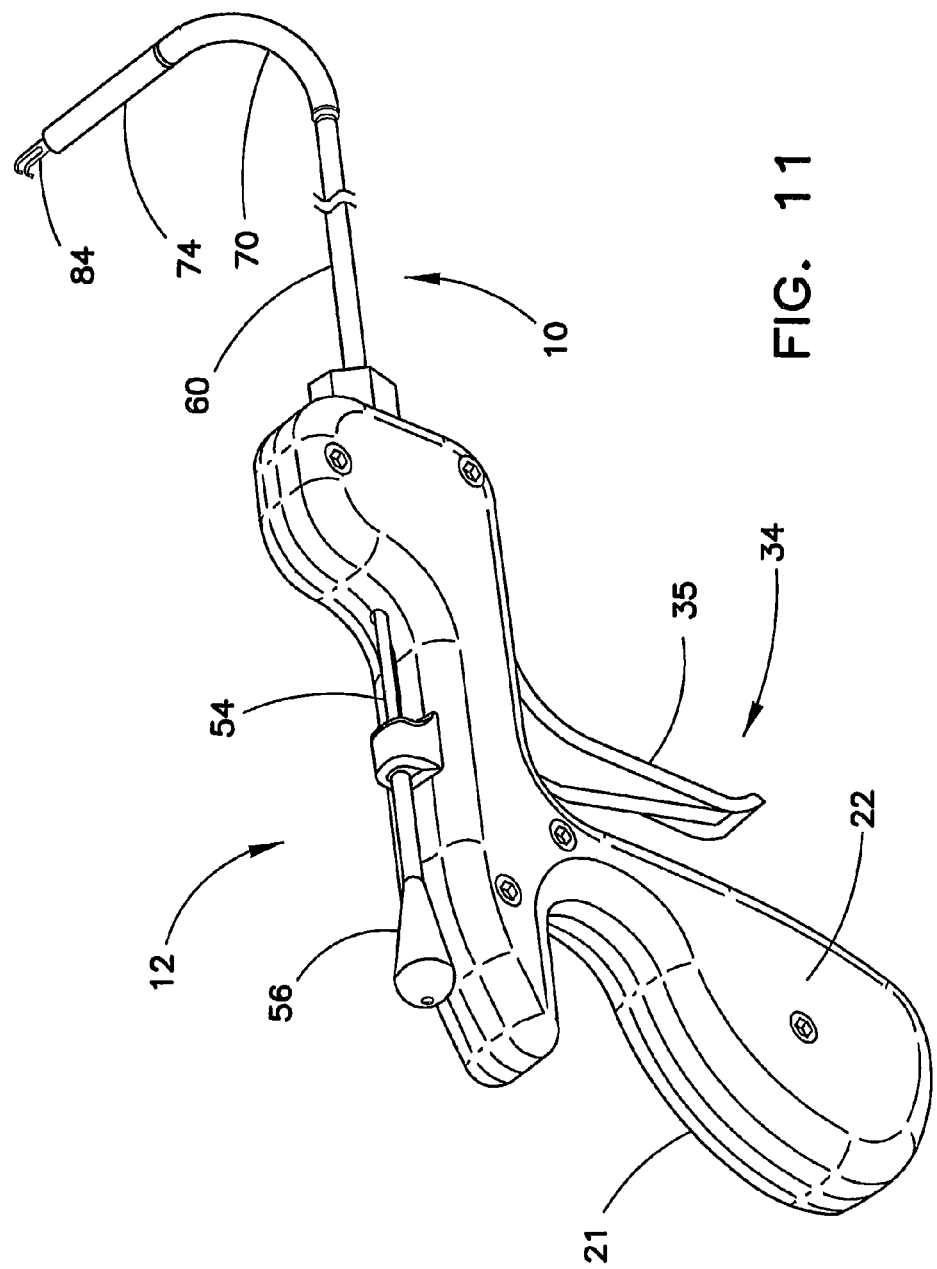
FIG. 11 illustrates the handle mechanism and the tip portion upon a retraction of the trigger, and the corresponding bending of the distal tip.

The handle 12 is then grasped by the hand of the operator in conventional fashion, and trigger grip 35 is pulled toward the operator (i.e., in a proximal direction), as shown in FIG. 11. As trigger grip 35 is pulled in the proximal direction, trigger extender 36 slides in the proximal direction along the interior of handle 12. The movement of trigger grip 35 and trigger extender 36 is best shown in FIGS. 4A and 4B. As trigger extender 36 is moved in the proximal direction, retriever pull wire 52 is pulled proximally in tandem with extender 36 (FIG. 5). As retriever pull wire 52 is pulled in the proximal direction, retriever flex tube 70 bends along the side of flex coil 78 occupied by the pull wire 52. See, e.g., FIGS. 7, 8 and FIG. 11.

Figure 12:
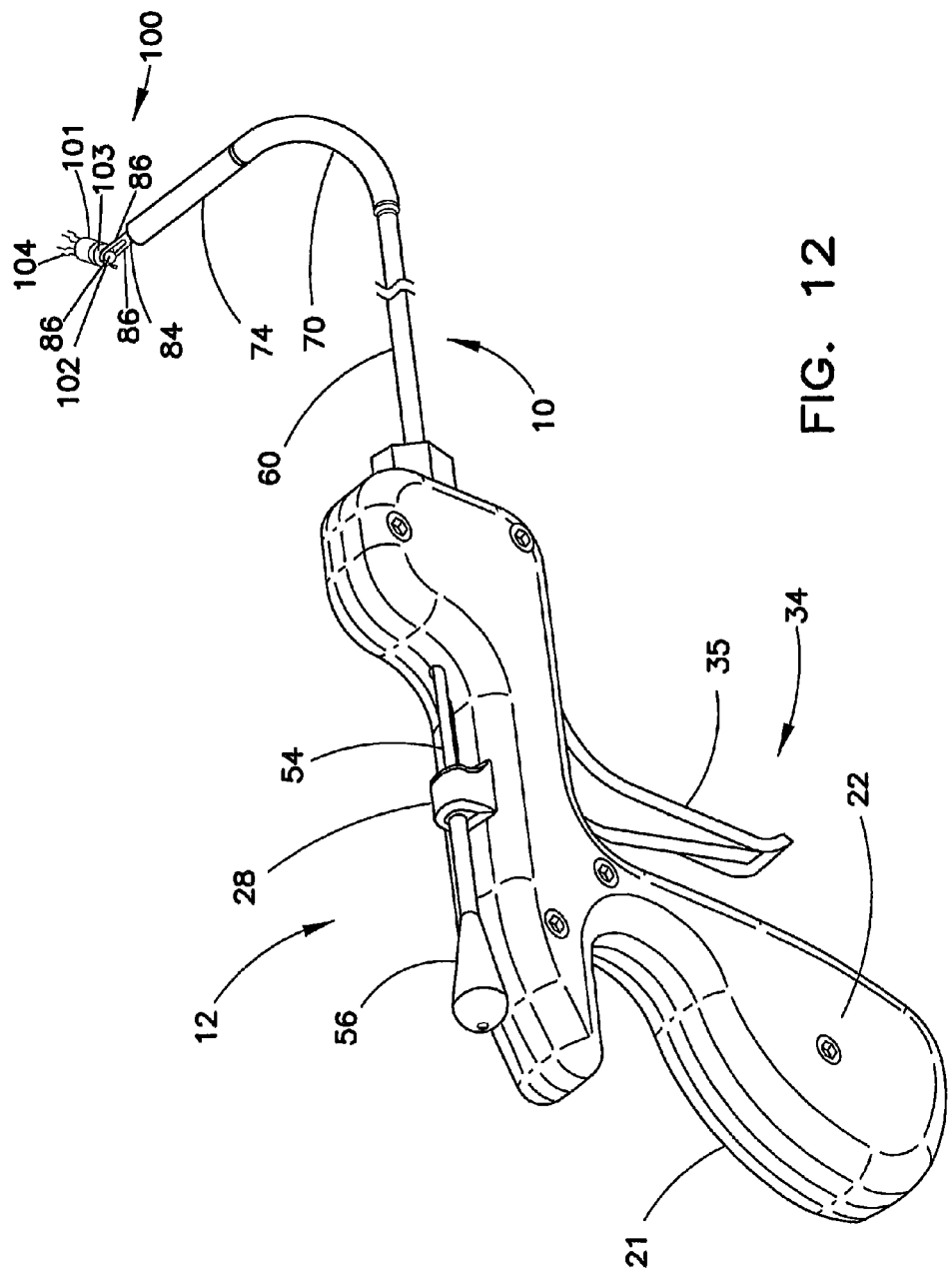
FIG. 12 illustrates the handle mechanism and tip portion as in FIG. 11, wherein the implanted apparatus is captured by the hook member.

Once hook member 84 is advanced to the vicinity of the implanted apparatus 100, the position of hook member 84, and therefore hook prongs 86, may be manipulated longitudinally and/or rotationally by suitable axial and/or rotational adjustment of manipulation knob 56, as stated above. The trigger grip 35 remains retracted, as shown in FIG. 12, as needed to achieve a degree of curvature of flex tube 70 suitable for reaching implanted apparatus 100. Under any suitable medical visualization means, such as fluoroscopy or ultrasound, knob 56 may be manipulated to enable the operator to steer the hook prongs 86 in a manner such that larger diameter element 102 of the implanted apparatus 100 may be grasped, snared, hooked, or otherwise engaged, as shown in FIG. 12. As described above, larger diameter element 102 is spaced from the main cylindrical body 101 of the implanted apparatus by smaller diameter extended, or neck, portion 103. Thus, in the present example, hook prongs 86 are manipulated to traverse opposing axial sides of extended, or neck, portion 103, and thereby grasp the implanted apparatus 100 at larger diameter element 102.

Figure 13:
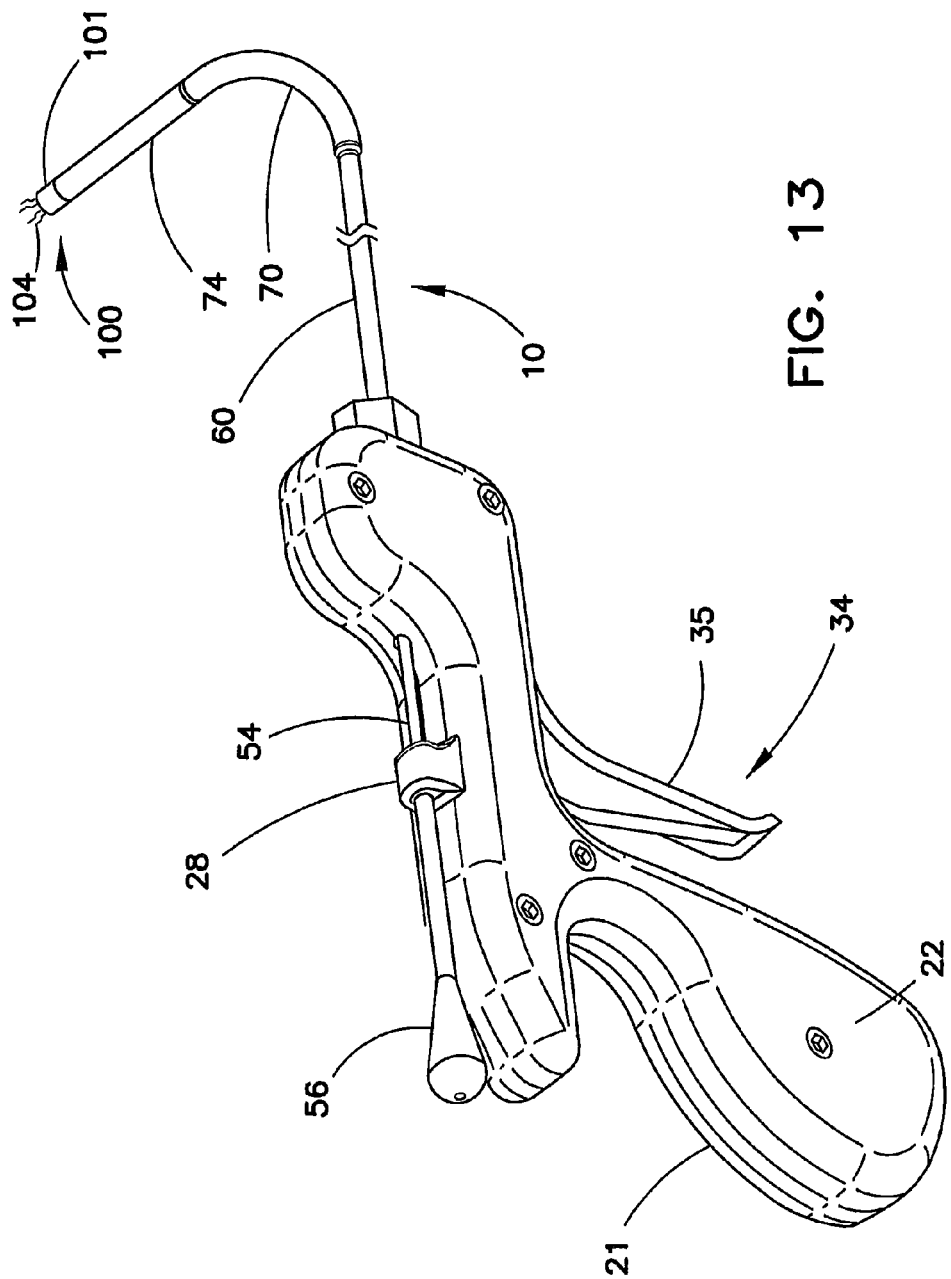
FIG. 13 illustrates the implanted apparatus partially drawn into the retrieving tip.

Once implanted apparatus 100 has been firmly engaged by hook member 84, manipulation knob 56 is withdrawn in the proximal direction (FIG. 13A) to draw implanted apparatus 100 into retrieving tip 74. In FIG. 13, implanted apparatus 100 is partially received within retrieving tip 74. Further withdrawal of manipulator knob 56 fully draws the implanted apparatus 100 into the retrieving tip 74. The snare having the implanted apparatus captured therein may then be withdrawn from the body passage.

Figure 14:
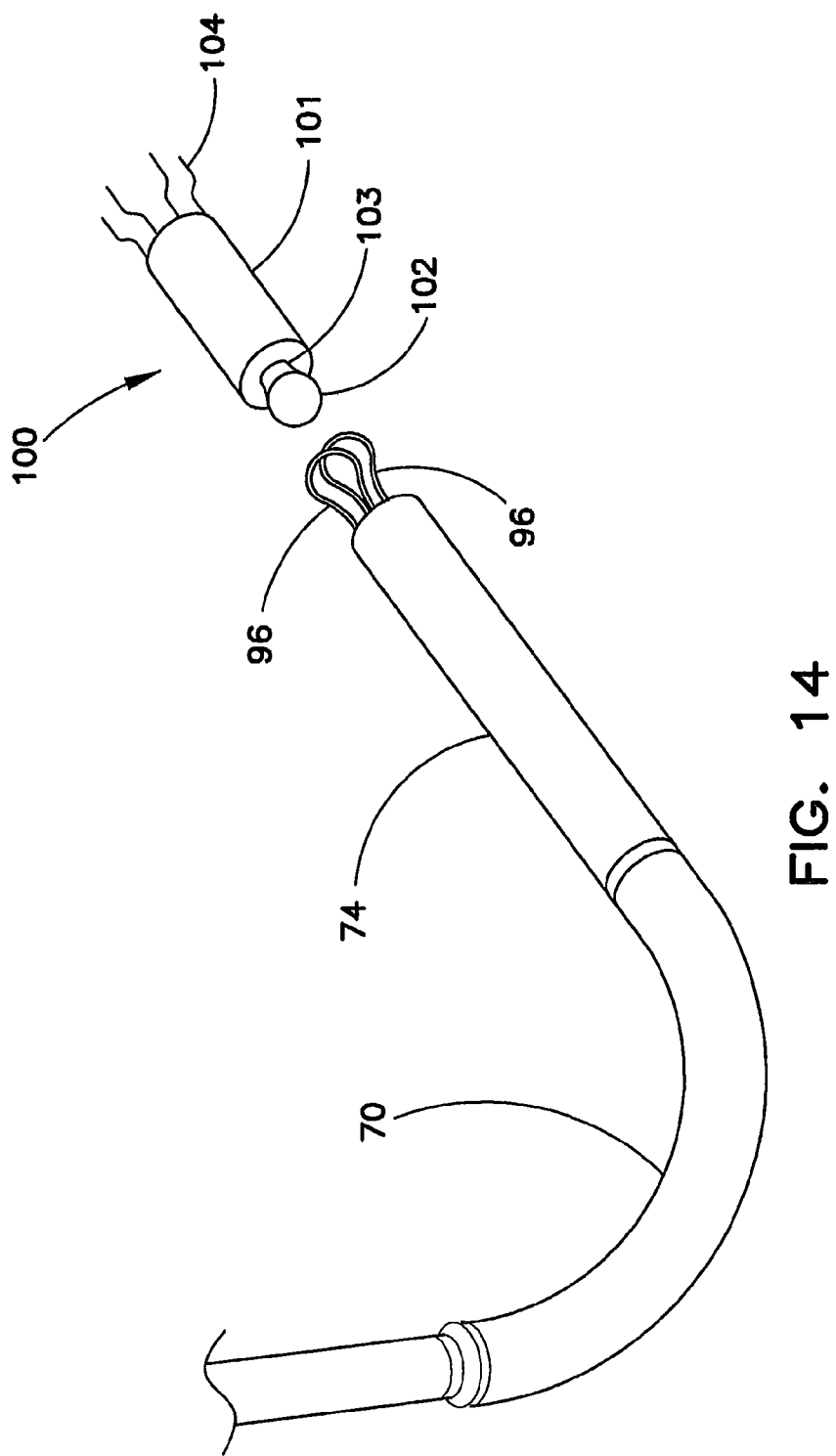
FIG. 14 illustrates a side view of the distal portion of a snare, illustrating an alternate version of the extendable member.
Figure 15:
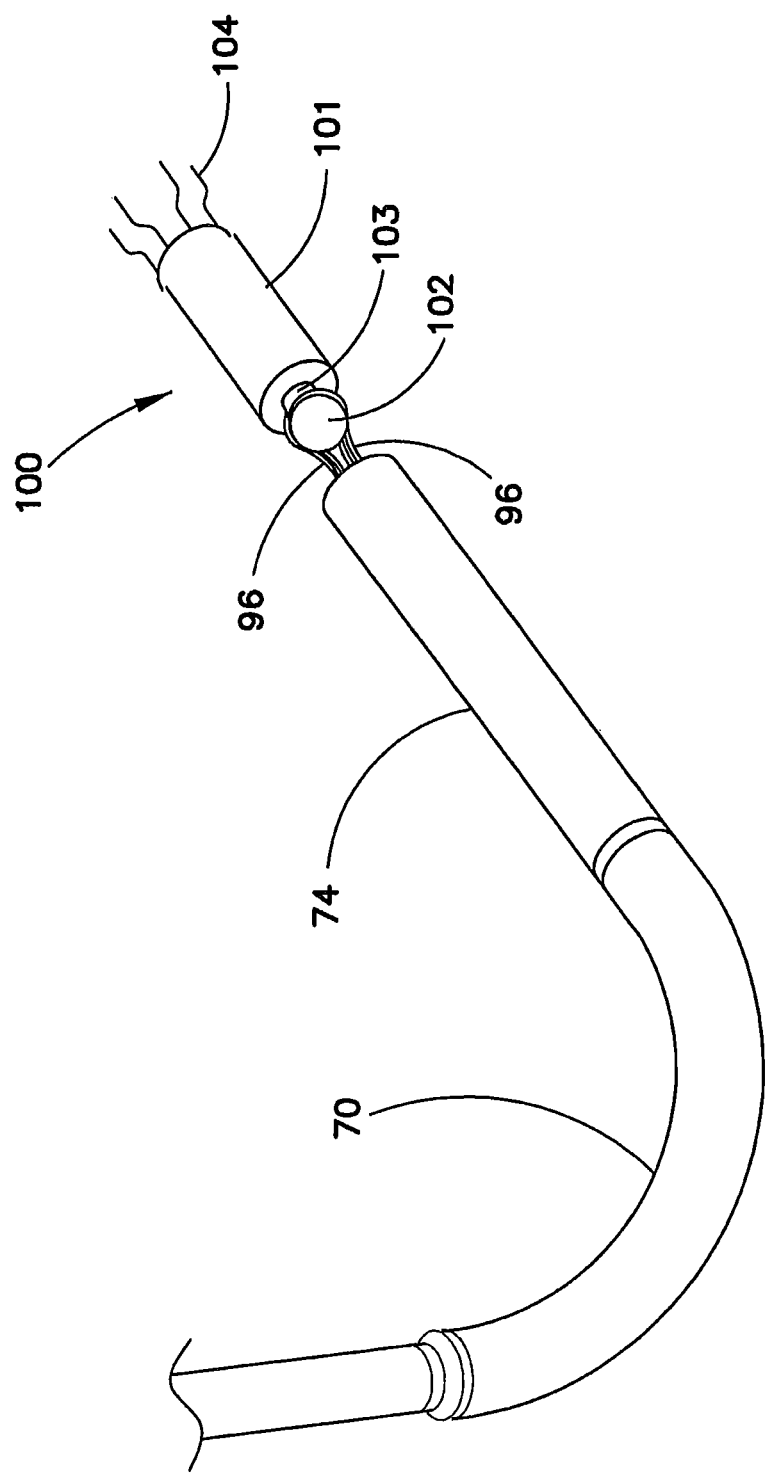
FIG. 15 illustrates the snare of FIG. 14 upon capture of the proximal end of the implantable apparatus.
Figure 15A:
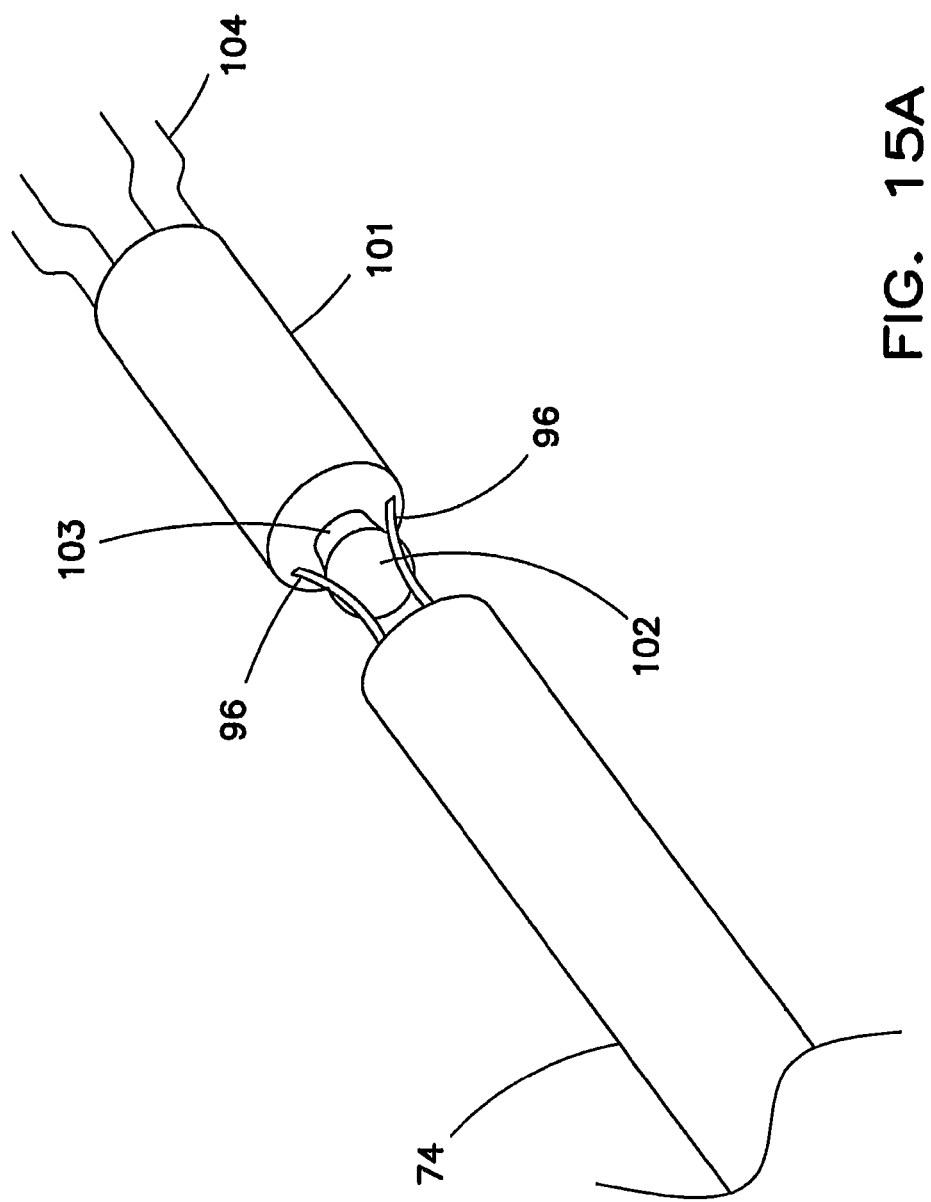
FIG. 15A illustrates the snare upon and implantable apparatus rotated about 90 degrees from the orientation as shown in FIG. 15.

Those skilled in the art will recognize that the extendable member of tip portion 16 may comprise structures other than dual-prong hook member 84 as described in the preceding example. FIGS. 14, 15, and 15A illustrate another example of an extendable member suitable for engagement with a larger diameter element 102 of implantable medical apparatus 100. In this example the extended member comprises dual paddles 96, 96. Paddles 96 may be arranged for engagement with a pusher 82 in any convenient manner, e.g., in the manner described above with regard to dual hooks 86, as shown in FIGS. 7, 8. As a result, paddles 96 are extendable from retrieving tip 74 in the same manner as the dual-prong hook member illustrated in the preceding figures.

As shown in FIGS. 14, 15, 15A each paddle 96 is configured to have an opening suitable for capturing larger diameter element 102 of implantable medical apparatus 100 as described. As with hook member 84, the paddles are preferably formed of a composition, e.g., stainless steel, titanium, nitinol, and the like, that renders the paddles visible under medical imaging techniques.

In the examples illustrated above, larger diameter element 102 of the implantable apparatus 100 has a generally bulbous, or spherical, ball-like shape. This shape is believed suitable for most applications, as the ball-like structure of the implanted apparatus does not provide recessed surfaces of the type that may otherwise allow, or promote, undesirable amounts of tissue growth around the element 102 during the period of implantation. Other suitable configurations that are also not conducive to such tissue growth include distally-tapered elements, and other geometrical designs functionally similar to the ball-like design. Configurations having exposed pockets, recessed surfaces, and the like (e.g., a mushroom-shaped element), while acceptable in some applications, may be less desirable in other applications as such configurations may provide surfaces that promote undesired tissue growth. As recognized by those skilled in the art, excessive tissue growth is undesirable, as it may obstruct or otherwise resist withdrawal of the apparatus into the snare tip.

The complementary design of the implantable apparatus comprising a body 101 having an extended portion 103 with a larger diameter element 102 at an end thereof, and a snare having an extendable member (such as the dual-prong hook member 84 or dual paddles 96 in the illustrated examples) that is capable of engaging, capturing, or otherwise controlling the position of the larger diameter element along dual surfaces as described, provides a self-centering feature to the snare system. By providing a structure that is capable of establishing control of the larger diameter element along dual surfaces at opposing sides of the element, apparatus 100 may be readily drawn directly into retrieving tip 74 (FIG. 13), in the substantial absence of sway and/or other lack of control exhibited by prior art hook, snag, loop, and like devices. Prior devices that only have a single or otherwise non-controlling area of contact between the snare tip and the implantable apparatus are not capable of the type of self-centering of the implantable apparatus during entry into the retrieving tip that is achievable with the extendable member as shown and described.

Although the examples provided above describe specific structures that are capable of such retrieval and control, other suitably-shaped structures may be substituted for the dual-prong hook and the paddles illustrated in the examples, as long as such structures are capable of self-centering the medical apparatus intended to be delivered to, or removed from, a target site as described. Generally, it is desirable that the extendable member be capable of controlling a position of the implantable apparatus from each side thereof, in the nature of the hook members or paddles shown and described. In this manner the medical apparatus can be readily captured, controlled, and/or drawn into, or delivered from, the retrieving tip in the substantial absence of sway, swing, or other lack of control as described above.

As stated hereinabove, the snare may be utilized to both retrieve an implantable apparatus from a body passageway, and to deliver, or deploy, an implantable apparatus to a target site within the body of the patient. As an additional feature, when the snare is used to deploy an apparatus, such as a pacemaker, for implantation, the pacing thresholds, signal amplitudes, etc., of the implanted apparatus can be measured in known fashion. If readings are not determined to be satisfactory, the apparatus can be re-deployed at a new location, and further readings can be taken. This can be repeated as many times as deemed necessary to achieve optimal readings. Such general techniques are known in the art and are further described, e.g., in U.S. Pat. Publ. No. 2007/0088418, incorporated by reference herein. However, additional efficiencies are achieved when such deployment is carried out utilizing a snare of the type described herein.

Those skilled in the art will also appreciate that the extended member, such as the hooks and paddles described, need not necessarily be arranged in the exact manner as described and illustrated herein. Rather, in an appropriate case, this arrangement can be reversed. That is, a larger diameter element (such as the ball-like bulbous element described) may be extendable from the retrieving tip in the same manner as the hooks and paddles described above. In this event, this extendable structure is configured for engagement with complementary structure (e.g., hooks or paddles) extending in a proximal direction from the implantable member.

The snare and the medical apparatus may be provided separately, or in combination as a snare system or a medical assembly. When provided as a snare system or medical assembly, the medical apparatus and the snare may be manufactured or otherwise sized and/or formed to include complementary features to facilitate capture and/or engagement of the medical apparatus and the snare. In addition, the respective snare tip and medical apparatus may have a complementary configuration such that the medical apparatus is easily receivable in, and/or deployable from, the snare tip. In the non-limiting examples shown and described herein, at least a portion of the length of the medical apparatus is provided with a generally cylindrical outer surface that is of generally complementary size and shape with the inner surface of the snare tip. A snare system or assembly as described hereinabove may be readily used for deploying the medical apparatus and/or retrieving the apparatus from the body of the patient.

It is intended that the foregoing detailed description be regarded as illustrative rather than limiting, and that it be understood that it is the following claims, including all equivalents, that are intended to define the spirit and scope of this invention.

The invention claimed is:

1. A snare for use with an implantable medical apparatus having a cylindrical body and a proximal interface portion extending from a proximal face of the cylindrical body, the proximal face being disposed within a plane perpendicular to a longitudinal axis of the cylindrical body, the snare comprising:

an elongated shaft having a proximal end, a distal end, and a passageway extending therethrough;

a tip having a proximal end, a distal end, and a passageway extending therethrough, said tip passageway aligned with said shaft passageway and sized such that said implantable apparatus is partially receivable therein, a length of said tip capable of flexure, said tip proximal end engaged with said shaft distal end, said tip including an extendable member configured for engagement with the proximal interface portion of said implantable apparatus, said extendable member selectively receivable in said tip passageway, deployable in a distal direction from said tip passageway, and rotatable relative to said tip passageway;

a handle configured for engagement with said shaft proximal end, said handle including an activator;

a wire member having a proximal end and a distal end, said proximal end engaged with said handle activator and said distal end engaged with said tip length capable of flexure, said wire member movable for flexure of said tip length upon a movement of said activator; and an elongated mechanism having a proximal portion engaged with said handle and a distal portion engaged with said tip extendable member, said elongated mechanism configured for selectively controlling said receiving, deploying, and rotating of said extendable member, wherein said tip comprises a proximal portion and a distal portion, said proximal portion comprising said tip length capable of flexure, said distal portion terminating in a distal end face and having a greater rigidity than said proximal portion, said distal end face being disposed within a plane perpendicular to a longitudinal axis of the distal portion of said tip, wherein said extendable member and the proximal interface portion of said implantable apparatus are both fully received within said distal portion, and wherein said proximal face of the cylindrical body is in contact with said distal end face of the distal portion.

2. The snare of claim 1, wherein said extendable member is structured for self-centering said implantable apparatus during said use.

3. The snare of claim 2, wherein the proximal interface portion of said implantable medical apparatus includes a smaller diameter extended portion extending proximally from said proximal face of the cylindrical body, and a larger diameter element at a proximal end of said smaller diameter extended portion, said larger diameter element having opposing sides, and wherein said extendable member is configured for engaging each of said opposing sides of said larger diameter element.

4. The snare of claim 1, wherein said activator comprises a trigger.

5. The snare of claim 1, wherein said proximal portion of said elongated mechanism comprises an elongated pusher member, and said distal portion comprises a coil.

6. The snare of claim 5, further comprising a retriever union member for joining a distal end of said elongated pusher member and a proximal end of said coil.

7. The snare of claim 6, further comprising a bend tab extending distally from said retriever union member along an exterior length of said coil.

8. The snare of claim 7, wherein said wire member distal end extends along an exterior length of said coil substantially opposite of bend tab.

9. The snare of claim 8, further comprising a stabilizing wire disposed interiorly of said coil, said stabilizing wire configured for minimizing a flexing of said coil.

10. The snare of claim 1, wherein the proximal face of the cylindrical body of said implantable medical apparatus has an outside diameter that is substantially equal to an outside diameter of the distal end face of the distal portion of said tip.

11. A snare system, comprising:
an implantable medical apparatus, the implantable medical apparatus comprising a main body portion and a graspable structure extending proximally from a proximal end face of said main body portion, the proximal end face being perpendicularly oriented relative to the main body portion; and
a snare configured for at least one of deploying said medical apparatus to an interior body surface of a patient, and retrieving said medical apparatus from said interior body surface, said snare comprising:
an elongated shaft having a proximal end, a distal end, and a passageway extending therethrough;
a tip having a proximal end, a distal end, and a passageway extending therethrough, said tip passageway aligned with said shaft passageway and sized such that said implantable apparatus is partially receivable therein, a length of said tip capable of flexure, said tip proximal end engaged with said shaft distal end, said tip including an extendable member configured for engagement with said graspable structure of said implantable apparatus, said extendable member selectively receivable in said tip passageway, deployable in a distal direction from said tip passageway, and rotatable relative to said tip passageway;
a handle configured for engagement with said shaft proximal end, said handle including an activator;
a wire member having a proximal end and a distal end, said proximal end engaged with said handle activator and said distal end engaged with said tip length capable of flexure, said wire member movable in a proximal direction for flexure of said tip length upon a movement of said activator; and
an elongated mechanism having a proximal portion engaged with said handle and a distal portion engaged with said tip extendable member, said elongated mechanism configured for selectively controlling said receiving, deploying, and rotating of said extendable member,
wherein said tip comprises a proximal portion and a distal portion, said proximal portion comprising said length capable of flexure, said distal portion comprising a distal end face and having a greater rigidity than said proximal portion, said distal end face being perpendicularly oriented relative to said tip distal portion, and wherein the graspable structure of said implantable medical apparatus is sized to be fully receivable within said distal portion such that proximal end face of said main body portion is engaged by and disposed against the distal end face of said tip.

12. The snare system of claim 11, wherein said snare is configured for both deploying said medical apparatus to said interior body surface, and retrieving said medical apparatus from said interior body surface.

13. The snare system of claim 11, wherein said graspable structure of said medical apparatus comprises a smaller diameter portion extending from the proximal end face of said main body portion, and a larger diameter element at a proximal end of the smaller diameter portion, and wherein said extendable member is sized and shaped for capture of said larger diameter element in a manner sufficient to self-center said medical apparatus relative to said tip passageway for receiving said implantable apparatus in said tip passageway.

14. The snare system of claim 13, wherein said larger diameter element has opposing sides, and wherein said extendable member comprises dual engagement elements, each of said elements configured for engaging a separate one of said opposing sides of said larger diameter element.

15. The snare system of claim 14, wherein said smaller diameter portion comprises a neck, and said larger diameter element comprises a ball member at the proximal end of the neck, and wherein said dual engagement elements comprise one of hooks and paddles.

16. The snare system of claim 11, wherein at least one of said implantable medical apparatus and said extendable member is visible under medical imaging.

17. The snare system of claim 11, wherein said activator comprises a trigger.

18. A medical assembly, comprising:
an implantable medical apparatus, the implantable medical apparatus comprising a main body portion having a proximal end face, said proximal end face being disposed perpendicularly to an outer surface of the main body portion, a neck portion extending in a proximal direction from the proximal end face of said main body portion, and a larger diameter element at a proximal end of said neck portion, said larger diameter element having opposing longitudinal sides; and a device configured for at least one of deploying said medical apparatus to an interior body surface of a patient, and retrieving said medical apparatus from said interior body surface, said device comprising:

an elongated shaft having a proximal end, a distal end, and a passageway extending therethrough;

a tip having a proximal end, a distal end, and a passageway extending therethrough, said tip passageway aligned with said shaft passageway and sized such that said implantable apparatus is partially received therein, a length of said tip capable of flexure, said tip proximal end engaged with said shaft distal end, said tip including an extendable member, said extendable member selectively received in said tip passageway, deployable in a distal direction from said tip passageway, and rotatable relative to said tip passageway, said extendable member comprising a first engagement element configured for controllably engaging a first one of said opposing sides of said larger diameter element, and a second engagement element for controllably engaging a second one of said opposing sides of said larger diameter element, said controllable engagement suitable for self-centering said implantable medical apparatus relative to said tip passageway;

a handle configured for engagement with said shaft proximal end, said handle including an activator;

a wire member having a proximal end and a distal end, said proximal end engaged with said activator and said distal end engaged with said tip length capable of flexure, said wire member movable in a proximal direction for flexure of said tip length upon a movement of said activator; and an elongated mechanism having a proximal portion engaged with said handle and a distal portion engaged with said tip extendable member, said proximal portion comprising a pusher member and said distal portion comprising a bendable coil, said elongated mechanism configured for selectively controlling said receiving, deploying, and rotating of said extendable member for effecting said controlled engagement of respective engagement elements with said opposing sides of said larger diameter element of said implantable medical apparatus, wherein at least one of said implantable medical apparatus and said extendable member is visible under medical imaging, and wherein said tip comprises a proximal portion and a distal portion, said proximal portion comprising said length capable of flexure, said distal portion having a greater rigidity than said proximal portion, wherein said extendable member is fully receivable within the distal portion, and wherein the neck portion and the larger diameter element of said main body portion are both fully received within the distal portion, and wherein the proximal end face of said main body portion is disposed against a distal end face of the distal portion, the distal end face being disposed perpendicularly to an outer surface of the tip distal portion.

* * * * *